US007868169B2

(12) United States Patent
Niddam-Hildesheim et al.

(10) Patent No.: US 7,868,169 B2
(45) Date of Patent: Jan. 11, 2011

(54) CRYSTALLINE ROSUVASTATIN INTERMEDIATE

(75) Inventors: Valerie Niddam-Hildesheim, Kadima (IL); Natalia Shenkar, Petach Tiqva (IL); Shlomit Wizel, Petah Tiqva (IL)

(73) Assignee: Teva Pharmaceutical Industries, Ltd., Petah Tiqva (IL)

(*) Notice: Subject to any disclaimer, the term of this patent is extended or adjusted under 35 U.S.C. 154(b) by 822 days.

(21) Appl. No.: 11/506,030

(22) Filed: Aug. 16, 2006

(65) Prior Publication Data

US 2007/0123550 A1     May 31, 2007

Related U.S. Application Data

(60) Provisional application No. 60/708,920, filed on Aug. 16, 2005, provisional application No. 60/710,930, filed on Aug. 23, 2005.

(51) Int. Cl.
  C07D 239/42    (2006.01)
  C07D 403/12    (2006.01)
(52) U.S. Cl. .................................... 544/332
(58) Field of Classification Search ............. 544/332
  See application file for complete search history.

(56) References Cited

U.S. PATENT DOCUMENTS

| | | | |
|---|---|---|---|
| 4,231,938 A | 11/1980 | Monaghan et al. |
| 4,346,227 A | 8/1982 | Terahara et al. |
| 4,444,784 A | 4/1984 | Hoffman et al. |
| 4,739,073 A | 4/1988 | Kathawala |
| 5,006,530 A | 4/1991 | Angerbauer et al. |
| 5,177,080 A | 1/1993 | Angerbauer et al. |
| 5,260,440 A | 11/1993 | Hirai et al. |
| 5,354,879 A | 10/1994 | Konoike et al. |
| RE37,314 E | 8/2001 | Hirai et al. |
| 6,316,460 B1 | 11/2001 | Creekmore et al. |
| 6,333,198 B1 | 12/2001 | Edmeades et al. |
| 6,777,552 B2 | 8/2004 | Niddam-Hildesheim et al. |
| 6,858,618 B2 | 2/2005 | Raza et al. |
| 2004/0009997 A1 | 1/2004 | Taylor et al. |
| 2005/0124639 A1 | 6/2005 | Narendra et al. |
| 2005/0131066 A1 | 6/2005 | Niddam-Hildesheim et al. |
| 2005/0159615 A1 | 7/2005 | Lifshitz-Liron et al. |
| 2005/0222415 A1 | 10/2005 | Kumar et al. |
| 2007/0037979 A1* | 2/2007 | Niddam-Hildesheim et al. ............... 544/330 |
| 2007/0123550 A1 | 5/2007 | Niddam-Hildesheim et al. |
| 2007/0167625 A1 | 7/2007 | Balanov et al. |

FOREIGN PATENT DOCUMENTS

| | | |
|---|---|---|
| CN | 1 733 774 | 2/2006 |
| CN | 1807417 | 7/2006 |
| CN | 1 872 841 | 12/2006 |
| EP | 0 521 471 | 1/1993 |
| EP | 0 554 455 | 8/1993 |
| EP | 0 850 902 | 7/1998 |
| EP | 0 984 011 | 3/2000 |
| JP | 07 118233 | 5/1995 |
| WO | WO 00/17150 | 3/2000 |
| WO | WO 00/49014 A | 8/2000 |
| WO | WO 01/60804 | 8/2001 |
| WO | WO 03/004455 | 1/2003 |
| WO | WO 03/016317 | 2/2003 |
| WO | WO 03/032995 | 4/2003 |
| WO | WO 03/087112 | 10/2003 |
| WO | WO 03/097614 A | 11/2003 |
| WO | WO 2004/014872 | 2/2004 |
| WO | WO 2004/052867 | 6/2004 |
| WO | WO 2004/108691 | 12/2004 |
| WO | WO 2005/021511 | 3/2005 |
| WO | WO 2005/023778 | 3/2005 |
| WO | WO 2006/035277 | 4/2006 |
| WO | WO 2006/079611 | 8/2006 |
| WO | WO 2006/100689 | 9/2006 |
| WO | WO 2006/106526 | 10/2006 |
| WO | WO 2006/136407 | 12/2006 |
| WO | WO 2006/136408 | 12/2006 |
| WO | WO 2007/007119 | 1/2007 |

OTHER PUBLICATIONS

Third Party Observations under Article 115 EPC in respect of European Patent Application No. EP06801964.5; Aug. 11, 2009.

Harwood, et al., "Experimental Organic Chemistry", 1989, pp. 127-132.

Anelli, et al., "Fast and Selective Oxidation of Primary Alcohols to Aldehydes or to Carboxylic Acids and of Secondary Alcohols to Ketones Mediated by Oxoammonium Salts Under Two-Phase Conditions", *J. Org. Chem.*, 1987, pp. 2559-2562, vol. 52, No. 12.

Hull, et al., "Quantification of Rosuvastatin in Human Plasma by Automated Solid-Phase Extraction Using Tandem Mass Spectrometric Detection", *Journal of Chromatography B: Biomedical Sciences & Applications*, 2002, pp. 219-228, vol. 772, No. 2.

Konoike, et al. "Practical Synthesis of Chiral Synthons for the Preparation of HMG-CoA Reductase Inhibitors" *J. Org. Chem.*, vol. 59, 1994, pp. 7849-7854.

Lenz, et al., "Tetra-*N*-Propylammonium Perruthenate (TPAP)-Catalysed Oxidations of Alcohols Using Molecular Oxygen As a Co-Oxidant", *J. Chem. Soc., Perkin Trans. 1*, 1997, 3291-3292.

Ley, et al., *Synthesis*, 1994, 639-666.

(Continued)

*Primary Examiner*—Venkataraman Balasubramanian
(74) *Attorney, Agent, or Firm*—Kenyon & Kenyon LLP

(57) ABSTRACT

Provided is a crystalline rosuvastatin intermediate and processes for preparation thereof.

28 Claims, 3 Drawing Sheets

OTHER PUBLICATIONS

Lipid Research Clinics Program, "The Lipid Research Clinics Coronary Primary Prevention Trial Results: I. Reduction in Incidence of Coronary Heart Disease", *J.A.M.A.*, 1984, 351-74, vol. 251, No. 3.

Loubinoux, et al., "The Enantioselective Synthesis of Simplified Southern-Half Fragments of Soraphen A", *Tetrahedron*, 1995, pp. 3549-3558, vol. 51, No. 12.

Ohrlein, et al., "Chemo-Enzymatic Approach to Statin Side-Chain Building Blocks", *Adv. Synth. Catal.*, 2003, pp. 713-715, vol. 345.

Scandinavian Simvastatin Survival Study Group, "Randomised Trial of Cholesterol Lowering in 4444 Patients With Coronary Heart Disease: The Scandinavian Survival Study (4s)", *The Lancet*, 1994, pp. 1383-1389, vol. 344.

Snyder, et al., *Introduction to Modern Liquid Chromatography, 2nd ed.*, John Wiley & Sons: New York, 1979, pp. 549, 552, 571-572.

Strobel, et al., *Chemical Instrumentation: A Systematic Approach, 3rd ed.*, Wiley & Sons: New York, 1989, pp. 391-393, 879, 894, 922, 924-925, 953.

Szantay, et al., "Synthesis of Novel HMG-CoA Reductase Inhibitors, Naphthalene Analogs of Mevinolin", *Liebigs Ann. Chem.*, 1992, pp. 145-157.

Theisen, P.D. et al., "Improved procedure for preparation of optically active 3-hydroxyglutarate monoesters and 3-hydroxy-5-oxoalkanoic acids," *Journal of Organic Chemistry*, vol. 53(10), 1988: 2374-2378.

Watanabe, Masamichi et al., "Synthesis and biological activity of methanesulfonamide pyrimidine- and N-methanesulfonyl pyrrole-substituted 3,5-dihydroxy-6-heptenoates, a novel series of HMG-CoA reductase inhibitors," *Bioorganic & Medicinal Chemistry*, 5(2), pp. 437-444, 1997.

Witztum, "Chapter 36: Drugs Used In The Treatment Of Hyperlipoproteinemias", *Goodman & Gilman's The Pharmacological Basis Of Therapeutics, 9th ed.*, pp. 875-897, 1996.

* cited by examiner

CRYSTALLINE ROSUVASTATIN INTERMEDIATE

RELATED APPLICATIONS

This application claims the benefit of provisional application Ser. No. 60/708,920, filed Aug. 16, 2005, and provisional application Ser. No. 60/710,930, filed Aug. 23, 2005, both of which are incorporated herein by reference.

FIELD OF THE INVENTION

The invention relates to a crystalline intermediate of rosuvastatin and a process for the preparation thereof.

BACKGROUND OF THE INVENTION

Rosuvastatin calcium (monocalcium bis (+) 7-[4-(4-fluorophenyl)-6-isopropyl-2-(N-methyl-N-methylsulfonylaminopyrimidin)-5-yl]-(3R,5S)-dihydroxy-(E)-6-heptenoate) is an HMG-CoA reductase inhibitor, developed by Shionogi for the once daily oral treatment of hyperlipidaemia (Ann Rep, Shionogi, 1996; Direct communications, Shionogi, 8 Feb. 1999 & 25 Feb. 2000). Rosuvastatin calcium has the following chemical formula:

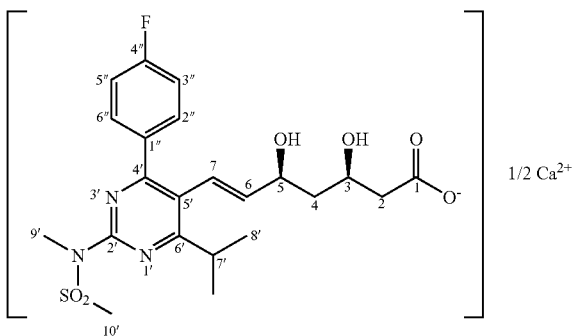

Rosuvastatin calcium is marketed under the name CRESTOR for treatment of a mammal such as a human. According to the maker of CRESTOR, it is administered in a daily dose of from about 5 mg to about 40 mg for LDL cholesterol reduction.

One of the key intermediates of the synthesis of Rosuvastatin calcium is "intermediate 21." "Intermediate 21" refers to t-butyl ester of (+)-7-(4-(4-fluorophenyl)-6-isopropyl-2-(N-methyl-N-methane-sulfonylaminopyrimidin)-5-yl)-3(R)hydroxy-5-oxo-(E)-6-heptenoic acid:

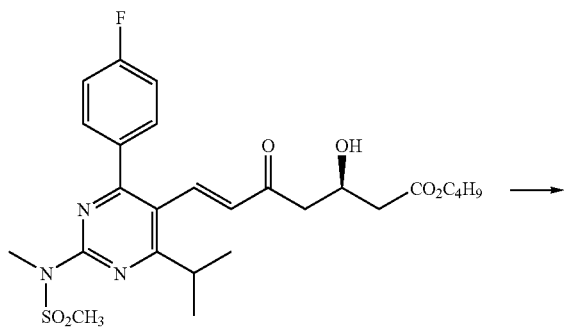

21

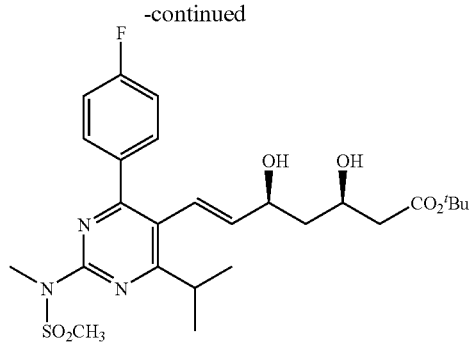

TBRE

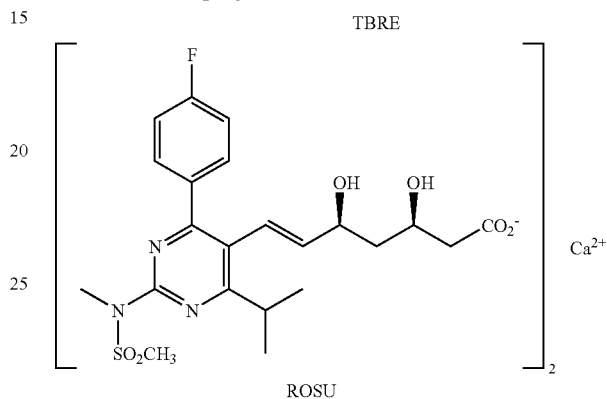

ROSU

In USRE37,314E, the corresponding methyl ester of intermediate 21 (rather than t-butyl ester) is described as a "syrup" after column chromatography. See example 1-(4). In WO03/097614, the same intermediate having a methyl ester is described as a "thick oil." See example 2, step b. In yet another reference, WO03/087112, column chromatography is carried out to purify intermediate 21.

Generally, an oil is difficult to handle and contains impurities. Furthermore, chromatography is not preferable for use on an industrial scale.

SUMMARY OF THE INVENTION

One embodiment of the invention provides a crystalline rosuvastatin intermediate or an enantiomer thereof having the following structure:

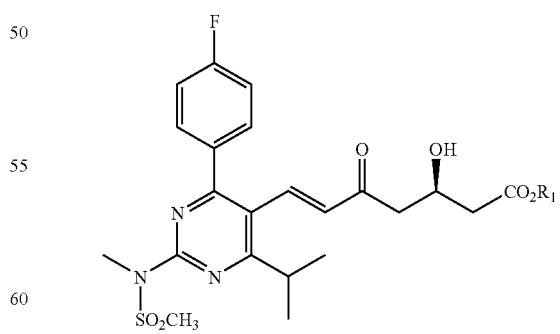

wherein $R_1$ in such crystalline rosuvastatin intermediate is a carboxy protecting group.

Another embodiment of the invention provides a process for preparing the above crystalline rosuvastatin intermediate including crystallizing the intermediate from a solution having at least one organic solvent.

A further embodiment of the invention provides a process for preparing rosuvastatin, rosuvastatin lactone or a pharmaceutically acceptable salt thereof including crystallizing the rosuvastatin intermediate:

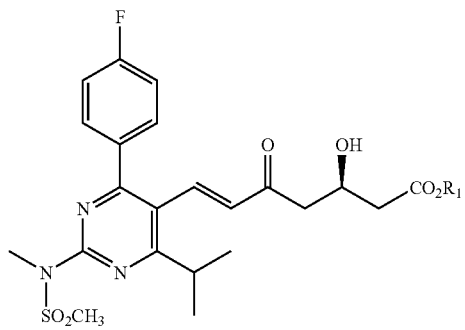

wherein $R_1$ is a carboxy protecting group, from a solution having at least one organic solvent, said organic solvent being optionally in mixture with water, and converting the crystalline intermediate to rosuvastatin, rosuvastatin lactone or a pharmaceutically acceptable salt thereof.

Another embodiment of the invention provides a pharmaceutical composition including rosuvastatin or a pharmaceutically acceptable salt thereof and at least one pharmaceutically acceptable excipient, wherein the rosuvastatin, rosuvastatin lactone or salt thereof is prepared by converting crystalline rosuvastatin intermediate having the following structure:

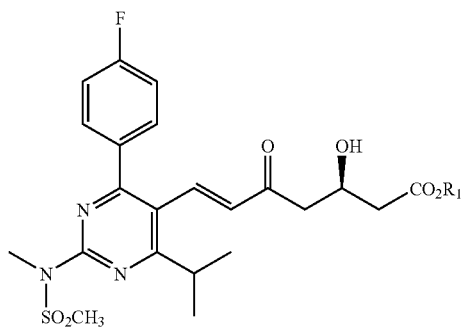

wherein $R_1$ is a carboxy protecting group, to rosuvastatin or a pharmaceutically acceptable salt thereof.

One embodiment of the invention provides a process of preparing the above pharmaceutical composition including mixing the rosuvastatin, rosuvastatin lactone or a pharmaceutically acceptable salt thereof with a pharmaceutically acceptably carrier.

One embodiment of the invention provides a method of lowering LDL levels in a mammal comprising administering the pharmaceutical composition of the invention to a mammal.

DETAILED DESCRIPTION OF THE INVENTION

Figure 1:
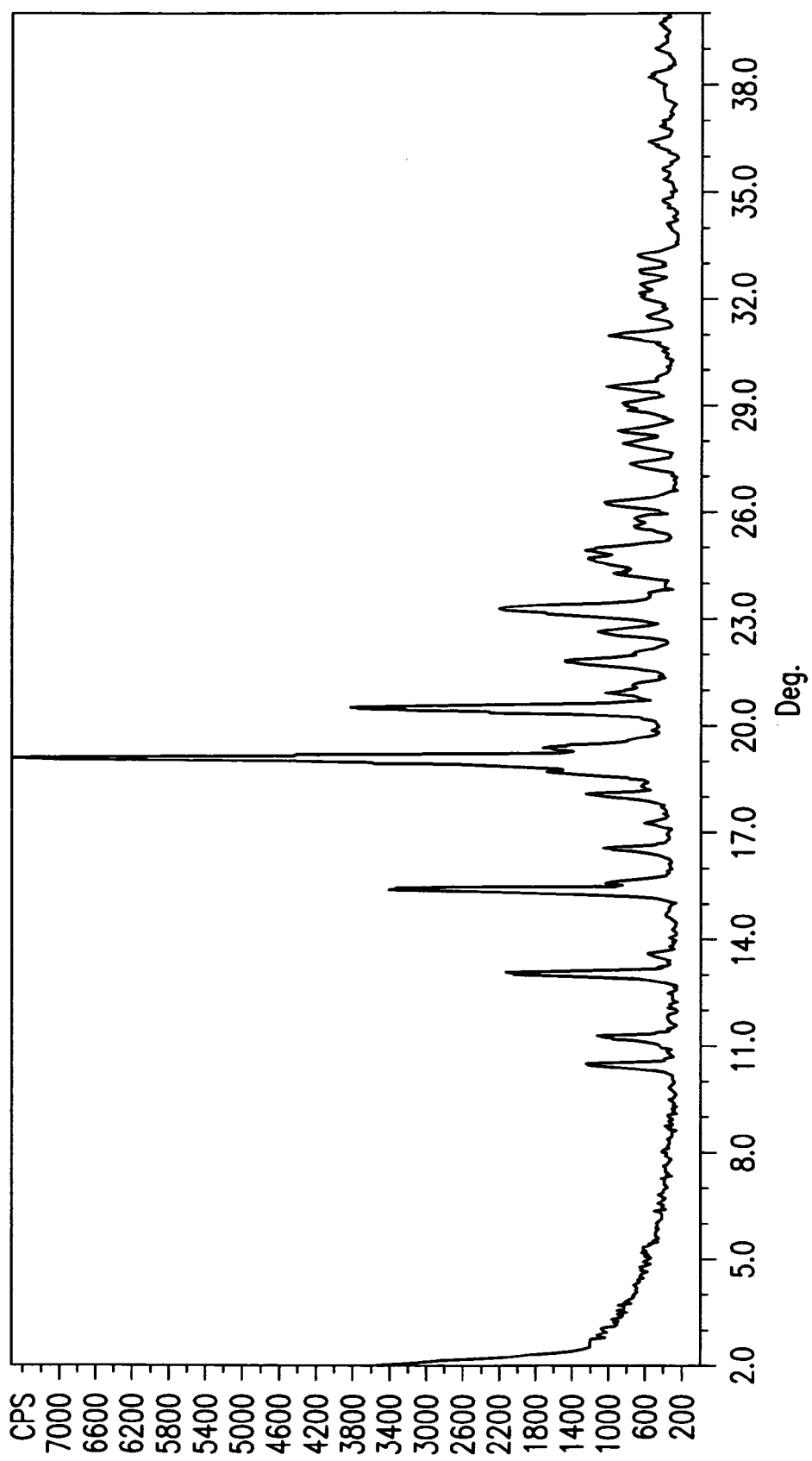
FIG. 1: X-Ray Powder Diffractogram of crystalline Rosuvastatin intermediate.
Figure 2:
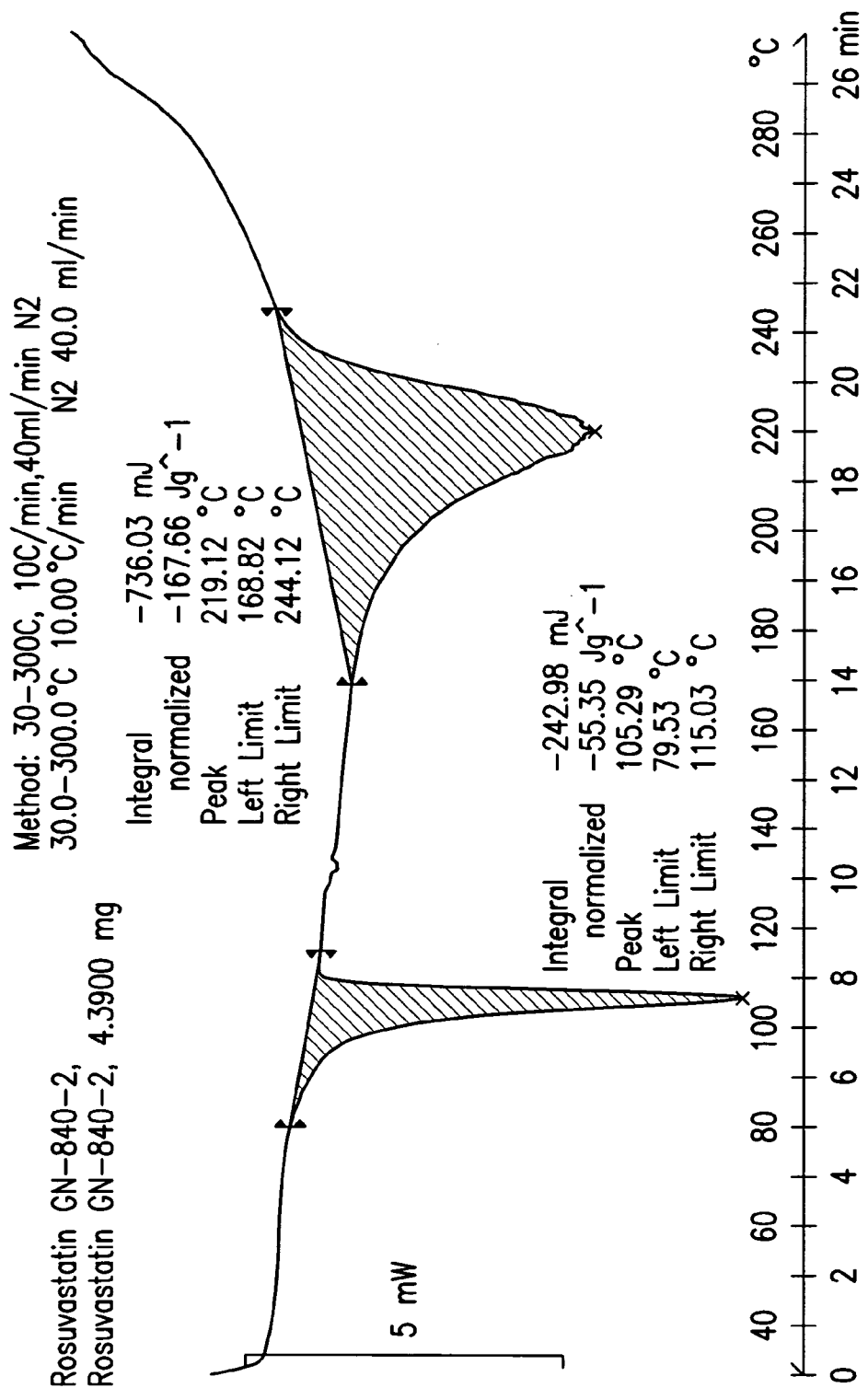
FIG. 2: DSC thermogram of crystalline Rosuvastatin intermediate.
Figure 3:
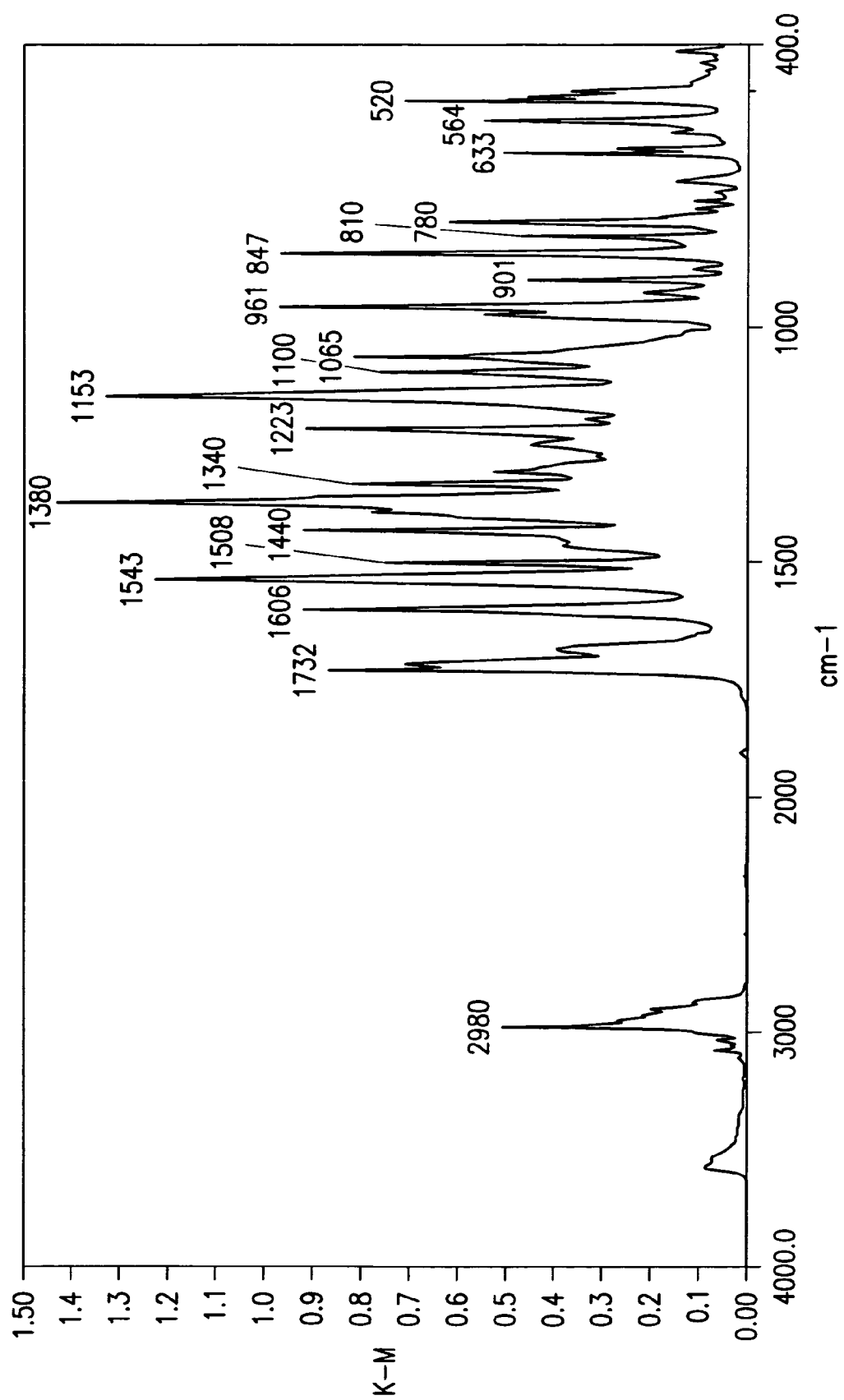
FIG. 3: FTIR spectrum of crystalline Rosuvastatin intermediate.

One embodiment of the invention provides a crystalline intermediate ("intermediate") or an enantiomer thereof, which is used for the synthesis of rosuvastatin, having the following structure:

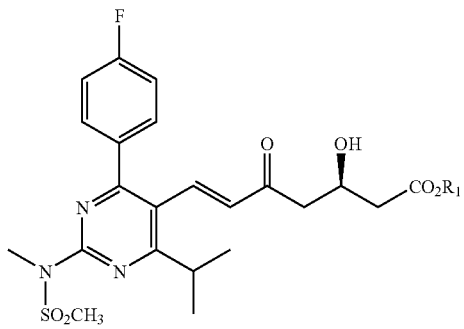

wherein $R_1$ in such crystalline rosuvastatin intermediate is a carboxy protecting group.

This crystalline intermediate is suitable for use on an industrial scale, inter alia because crystalline forms may be easier to handle and process than oil intermediates. Crystallization also allows for purification of the intermediate.

$R_1$ in the crystalline rosuvastatin intermediate may be any suitable carboxy protecting group, including but not limited to phenyl. Preferably, $R_1$ in the crystalline rosuvastatin intermediate is a $C_1$ to $C_4$ alkyl group. In one embodiment, $R_1$ is a methyl group.

In a preferred embodiment, $R_1$ is a tert-butyl, providing "intermediate 21":

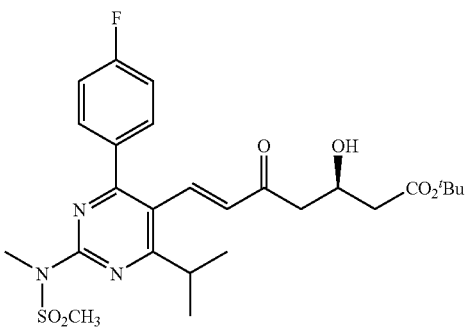

The crystallization and isolation of intermediate 21 is illustrated in the examples.

The crystallinity of the intermediate 21 is confirmed by powder X-Ray Diffraction. Crystalline rosuvastatin intermediate 21 may be characterized by powder x-ray diffraction peaks at 10.5, 13.1, 15.4, 19.0, and 20.4±0.2 degrees two theta. Crystalline rosuvastatin intermediate 21 may be further characterized by powder x-ray diffraction peaks at 11.2, 15.7, 16.6, 18.0, 18.6, 19.4, 21.8, and 23.1±0.2 degrees two theta.

Crystalline rosuvastatin intermediate 21 may be characterized by an FTIR spectrum having peaks at 1543, 1380, 1153, 961, and 847 cm$^{-1}$. The compound may further be characterized by an FTIR spectrum having peaks at 2980, 1606, 1508, 1440, 1340, 1223, 1100 and 1065 cm$^{-1}$.

DSC thermogram for crystalline rosuvastatin intermediate 21 shows an endothermic peak at about 100° C., and a broad endotherm at about 220° C.

The intermediate, including intermediate 21, may be obtained as a solid by crystallization from a solution. The solution may be that of the intermediate in one or more organic solvents, or one or more water-miscible organic solvents in a mixture with water.

Examples of suitable solvents for crystallization include $C_6$ to $C_{12}$ aromatic and $C_5$ to $C_{12}$ aliphatic hydrocarbons, $C_3$ to $C_8$ ethers, $C_3$ to $C_8$ esters, $C_3$ to $C_8$ ketones, $C_1$ to $C_5$ alcohols, $C_1$ to $C_6$ alkylnitriles, and $C_1$ to $C_6$ alkylethers of ethylene glycol. Specific examples of solvents include toluene, n-heptane, n-hexane, cyclohexane, cellosolve, ethyl acetate, n-butyl acetate, t-butyl acetate, methyl t-butyl ether, di-ethyl ether, tetrahydrofuran, methanol, ethanol, isopropanol, n-butanol, methyl iso-butyl ketone, diethyl carbonate, butyl lactate, acetone, acetonitrile, mixtures thereof, and mixtures of any of these water miscible organic solvents with water. An example of a water miscible solvent for use as a mixture with water is methanol.

In a typical crystallization process, the intermediate is dissolved in one of the solvents, or the mixture of the solvents as provided above. To obtain the solution, the solvent may have to be heated. Heating is preferably carried out to a temperature of about 40° C. to about 100° C., and more preferably to a temperature of about 40° C. to about 70° C. The solution is then preferably allowed to cool, such to a temperature of about 20° C. to about 30° C., or room temperature. The solution may then be seeded. After seeding, the reaction mixture, which may be a slurry, may be further cooled, preferably to a temperature of about –10° C. to about 20° C. The crystallization process may be carried out overnight, i.e., for about 8 hours.

In one embodiment, the crystallization process includes heating the solvent to a temperature of about 40° C. to about 70° C. to obtain a solution, cooling the solution to a temperature of about 20° C. to about 30° C., seeding, cooling after seeding to a temperature of about –10° C. to about 20° C. and recovering the crystalline form.

The crystallization may result in a sticky solid, as in example 4. In such instance, such solid may be recrystallized or slurried.

Crystallization may include adding an anti-solvent to facilitate the precipitation of the intermediate. The term "anti-solvent" refers to a liquid that, when added to a solution of intermediate in a solvent, induces precipitation of intermediate. The anti-solvent may also be in a binary mixture with the solvent when the solution is prepared. Precipitation of intermediate 21 is induced by the anti-solvent when addition of the anti-solvent causes the intermediate to precipitate from the solution more rapidly or to a greater extent than the intermediate precipitates from a solution containing an equal concentration of the intermediate in the same solvent when the solution is maintained under the same conditions for the same period of time but without adding the anti-solvent. Suitable anti-solvents include water and $C_5$-$C_{12}$ cyclic or acyclic saturated hydrocarbons. Preferred anti-solvents include water, heptane, and hexane.

The resulting crystals are then recovered by conventional techniques, such as filtration. They may be washed with water or an organic solvent. The crystals are then preferably dried. The temperature may be increased or the pressure reduced to accelerate the drying process. Drying may be carried out at a temperature of about 40° C. to about 100° C., under a pressure of below about 100 mmHg. Preferably, drying occurs at a temperature of about 40° C. to about 60° C. Drying may also be performed under atmospheric pressure until constant weight.

The crystalline intermediate can be used to make rosuvastatin. The intermediate, which is in the form of a keto ester, is reduced to a diol ester. The reduction of the ketoester is disclosed in the art. See e.g. US2005/0159615, incorporated herein by reference in regard to its processes for reduction of statins. Reagents such as RU-binap, $EtB_3$/$NaBH_4$, MeO-9-BBN/$NaBH_4$ and diethylmethoxyborane/$NaBH_4$ may be used for the reduction.

The diol ester may be further converted into a pharmaceutically acceptable salt of the statin or a lactone. For example, the diol ester obtained may be reacted with sodium or calcium hydroxide to obtain the sodium or calcium salt. It is also possible to first obtain the sodium salt by reaction with sodium hydroxide, and then convert the sodium salt to calcium salt by using a source of calcium such as calcium chloride or calcium acetate. The basic hydrolysis of the statin diol-ester may be carried out with one or more equivalents of an alkali metal or alkaline earth metal base such as NaOH or $Ca(OH)_2$, in organic solvents such as $C_3$ to $C_8$ ethers (tetrahydrofuran, isopropyl ether), ACN (acetonitrile), $C_1$ to $C_5$ alcohols (MeOH, EtOH, IPA (isopropyl alcohol), propanol, butanol etc.), $C_3$ to $C_8$ ketones or esters (acetone, methyl ethyl ketone, methyl isopropyl ketone, ethyl acetate). The hydrolysis may also be carried out with water, a mixture of the above solvents, or a mixture of water and the above solvents, preferably at room temperature or by heating.

The present invention comprises pharmaceutical composition comprising rosuvastatin lactone or a pharmaceutically acceptable salts, and at least one pharmaceutically acceptable excipient.

The present invention further encompasses a process for preparing a pharmaceutical formulation comprising combining rosuvastatin lactone and pharmaceutically acceptable salt with at least one pharmaceutically acceptable excipient.

The present invention further encompasses the use of rosuvastatin lactone and pharmaceutically acceptable salts for the manufacture of a pharmaceutical composition.

The compositions of rosuvastatin, preferably rosuvastatin lactone and pharmaceutically acceptable salts, more preferably rosuvastatin calcium are prepared by mixing a pharmaceutically acceptable excipient with rosuvastatin (or a pharmaceutically acceptable salt thereof), wherein said rosuvastatin is prepared from the intermediate in crystalline form.

Pharmaceutical compositions of the invention include excipients. Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®, pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the invention, rosuvastatin and any other solid excipients are dissolved or suspended in a liquid carrier such as water, vegetable oil, alcohol, polyethylene glycol, propylene glycol or glycerin. Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxyl toluene, butylated hydroxyanisole and ethylenediamine tetraacetic acid may be added at levels safe for ingestion to improve storage stability.

According to the invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs. The dosage form of the invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the invention may comprise any of the aforementioned blends and granulates that were described with reference to tableting, however, they are not subjected to a final tableting step. The oral dosage form of the invention is preferably in the form of an oral capsule having a dosage of about 5 mg to about 40 mg, more preferably capsules of 5, 10, 20 and 40 mg.

Solid-State Characterization

Rosuvastatin intermediate of the invention was characterized by X-Ray powder diffraction (XRD), DSC analysis and FTIR spectroscopy.

XRD

XRD Diffractograms were collected on Scintag X-Ray powder diffractometer model X'TRA, Cu-tube, solid state detector. Scanning parameters: Range: 2-40 deg.2θ: continuous scan, Rate: 3.00 deg./min.

Thermal Analysis

Differential Scanning Calorimetry was performed on DSC821e, Mettler Toledo.

The crucible was crimped and punched prior to analysis. Experimental Conditions: Sample weight: 3-5 mg. Heating rate: 10° C./min.

FTIR Spectroscopy

FTIR spectrum was recorded on Perkin-Elmer spectrum One Spectrometer, Diffuse Reflectance Technique.

The Sample was finely ground with Potassium bromide, and the spectrum was recorded using Potassium Bromide background in a diffused reflectance accessory.

EXAMPLES

"TB21" refers to the t-butyl ester of intermediate 21

Example 1

Crystallization of TB21 in Toluene

TB21 (1.3 g, 56% assay, oil) was dissolved in toluene (1.5 ml) by heating to 60° C. until homogenization. The solution was then allowed to cool to room temperature, and seeding was performed. The mixture was stirred at this temperature overnight, not causing any precipitation. The solution was then cooled to 0° C., causing precipitation. The solid was then filtered under reduced pressure, washed with some drops of toluene and dried at 50° C. under reduced pressure for 18 hrs to get solid TB21 (0.20 g).

Example 2

Crystallization of TB21 in EtOAc

TB21 (1.76 g, 56% assay, oil) was dissolved in EtOAc (1.5 ml) by heating to 60° C. until homogenization. The solution was then allowed to cool to room temperature, and seeding was performed. The mixture was stirred at this temperature overnight. No precipitation was observed. The solution was then cooled to 0° C., causing precipitation. The solid was then filtered under reduced pressure, washed with some drops of EtOAc and dried at 50° C. under reduced pressure for 18 hrs to get solid TB21 (0.35 g).

Example 3

Crystallization of TB21 in MeOH

TB21 (1.25 g, 56% assay, oil) was dissolved in MeOH (1.5 ml) by heating to 60° C. until homogenization. The solution was then allowed to cool to room temperature, and seeding was performed. The mixture was stirred at this temperature overnight. No precipitation was observed. The solution was then cooled to 0° C., causing precipitation. The solid was then filtered under reduced pressure, washed with some drops of MeOH and dried at 50° C. under reduced pressure for 18 hrs to get solid TB21 (0.45 g).

Example 4

Crystallization of TB21 in MeOH:$H_2O$

TB21 (20 g, 56% assay, oil) was dissolved in MeOH (20 ml) and $H_2O$ (4 ml) at 40° C. The solution was then allowed to cool to 35° C., and seeding was performed. The mixture was allowed to cool to room temperature, and after about 30 minutes starts precipitation. After being stirred at this temperature overnight, the precipitate turned into a sticky semi-solid. The mixture was then heated to 35° C. and MeOH (5 ml) was added, so the sticky solid was dissolved. The slurry was then allowed to cool to room temperature, and stirred at this temperature for 2 hours. The solid was then filtered under reduced pressure, washed few drops of MeOH:$H_2O$ (5:1) and dried at 50° C. under reduced pressure until constant weight to get solid TB21 (5.86 g).

Example 5

Crystallization of TB21 in MTBE (Methyl t-Butyl Ether)

TB21 (2 g, 56% assay, oil) was dissolved in MTBE (2 ml) under heating to reflux. The solution was then allowed to cool to room temperature, and seeding was performed causing precipitation. The mixture was stirred at this temperature overnight, and then cooled to 0° C. for about 3 hours. The solid obtained was filtered under reduced pressure, washed with some drops of MTBE and dried at 50° C. under reduced pressure for 18 hrs to get solid TB21 (0.48 g).

Example 6

Crystallization of TB21 in IPA

TB21 (2 g, 56% assay, oil) was dissolved in IPA (2 ml) by heating to 70° C. until homogenization. The solution was then allowed to cool to room temperature, and seeding was performed. Precipitation starts about 1 hour after seeding. The mixture was stirred at room temperature overnight. The slurry was then cooled to 0° C. for about 30 minutes. The solid so-obtained was filtered under reduced pressure, washed with some drops of IPA and dried at 50° C. under reduced pressure for 72 hrs to get solid TB21 (0.45 g).

Example 7

Crystallization of TB21 in n-BuOH

TB21 (2 g, 56% assay, oil) was dissolved in n-BuOH (2 ml) by heating to 70° C. until homogenization. The solution was then allowed to cool to room temperature, and seeding was performed. No precipitation was observed. The solution was then cooled to 0° C., causing precipitation. The slurry was stirred at this temperature for about 30 minutes. The solid was then filtered under reduced pressure, washed with few drops of n-BuOH and dried at 50° C. under reduced pressure for 72 hrs to get solid TB21 (0.25 g).

Example 8

Crystallization of TB21 in MIBK (Methyl-isobutyl Ketone)

TB21 (2 g, 56% assay, oil) was dissolved in MIBK (2 ml) by heating to 60° C. until homogenization. The solution was then allowed to cool to room temperature, and seeding was performed. No precipitation was observed. The solution was then cooled to 0° C. and seeded. No precipitation was observed. The mixture was stirred at room temperature overnight, and after this time there is precipitation. The slurry was then cooled to 0° C. for 2 hrs, then filtered under reduced pressure, washed with few drops of MIBK and dried at 50° C. under reduced pressure for 18 hrs to get solid TB21 (0.09 g).

Example 9

Crystallization of TB21 in Diethyl Carbonate

TB21 (2 g, 56% assay, oil) was dissolved in DEC (2 ml) by heating to 60° C. until homogenization. The solution was then allowed to cool to room temperature, and seeding was performed. No precipitation was observed. The solution was then cooled to 0° C. and new seeding at this temperature induced precipitation. The slurry was stirred at room temperature overnight and then cooled to 0° C. for 2 hrs. The solid so-obtained was filtered under reduced pressure, washed with few drops of DEC and dried at 50° C. under reduced pressure for 18 hrs to get solid TB21 (0.36 g).

Example 10

Crystallization of TB21 in Butyl Lactate

TB21 (2 g, 56% assay, oil) was dissolved in Butyl lactate (2 ml) at 100° C. until homogenization. The solution was then allowed to cool to room temperature and seeded. No precipitation was observed. The solution was then cooled to 0° C. and new seeding at this temperature did not induced precipitation. The mixture was stirred at room temperature overnight and precipitation was observed. The slurry was cooled to 0° C. for 2 hrs. The solid was then filtered under reduced pressure, washed with few drops of Butyl lactate and dried at 50° C. under reduced pressure for 18 hrs to get solid TB21 (0.20 g).

Example 11

Crystallization of TB21 in MeOH:$H_2O$

TB21 (2 g, 56% assay, oil) was dissolved in MeOH:H2O (5:1, 2 ml) by heating to 55° C. until homogenization. The solution was then allowed to cool to room temperature and seeded. Precipitation was observed. The mixture was stirred at room temperature overnight, and then cooled to 0° C. for 2 hrs. The solid so-obtained was filtered under reduced pressure, washed with few drops of MeOH:$H_2O$ (5:1) and dried at 50° C. under reduced pressure for 18 hrs to get solid TB21 (0.73 g).

Example 12

Crystallization of TB21 in n-Butyl Acetate

TB21 (2 g, 56% assay, oil) was dissolved in n-BuOAc (2 ml) under heating. The solution was then allowed to cool to room temperature and seeding was performed causing precipitation. The mixture was then stirred at room temperature overnight, and then cooled to 0° C. for 2 hrs. The solid so-obtained was filtered under reduced pressure, washed and dried at 50° C. under reduced pressure for 18 hrs to get solid TB21 (0.25 g %).

Example 13

Crystallization of TB21 in IPA:$H_2O$

TB21 (2 g, 56% assay, oil) was dissolved in IPA(2.5 ml) and $H_2O$ (1 ml) by heating to 55° C. until homogenization. The solution was then allowed to cool to room temperature and seeding was performed. No precipitation was observed. The mixture was stirred at room temperature overnight and precipitation was observed. The slurry was then cooled to 0° C. for 2 hrs. The solid so-obtained was filtered under reduced pressure, washed with few drops of IPA:$H_2O$ (2.5:1) and dried at 50° C. under reduced pressure for 18 hrs to get solid TB21 (0.67 g).

Example 14

Crystallization of TB21 in MeOH:$H_2O$

TB21 (10.68 g, 56% assay, oil) was dissolved in MeOH:$H_2O$ (5:1, 5 ml) under heating, until homogenization. The solution was then allowed to cool to room temperature and seeding was performed. No precipitation was observed. The mixture was stirred at room temperature for 72 hours giving a thick slurry. The solid so-obtained was filtered under reduced pressure, washed with few drops of MeOH:$H_2O$ (5:1) and dried at 50° C. under reduced pressure for 18 hrs to get solid TB21 (6.33 g).

Example 15

Crystallization of TB21 in MTBE

TB21 (10 g, 56% assay, oil) was dissolved in MTBE (5 ml) by heating to reflux until homogenization. The solution was then allowed to cool to room temperature, and seeding was performed. No precipitation was observed. The mixture was stirred at room temperature for 72 hours giving a thick slurry. The solid was then filtered under reduced pressure, washed with some drops of MTBE and dried at 50° C. under reduced pressure for 18 hrs to get solid TB21 (4.5 g)

Example 16

Crystallization of TB21 in Acetone:$H_2O$

TB21 (2 g, 56% assay, oil) was dissolved in acetone (1 ml) and $H_2O$ (0.5 ml) by heating to 60° C. until homogenization. The solution was then allowed to cool to room temperature, and seeding was performed. No precipitation was observed. The mixture was stirred at room temperature for 18 hours. After this time, precipitation was observed. The slurry was then cooled to −10° C. for 2 hours. The solid was then filtered under reduced pressure, washed with some drops of Acetone:H$_2$O (2:1) and dried at 50° C. under reduced pressure for 18 hrs to get solid TB21 (0.63 g)

Example 17

Crystallization of TB21 in ACN:H$_2$O

TB21 (2 g, 56% assay, oil) was dissolved in ACN (1 ml) and H$_2$O (0.5 ml) by heating to 70° C. until homogenization. The solution was then allowed to cool to room temperature, and seeding was performed. No precipitation was observed. The mixture was stirred at room temperature for 18 hours. After this time, precipitation was observed. The slurry was then cooled to −10° C. for 2 hours. The solid was then filtered under reduced pressure, washed with some drops of ACN:H$_2$O (2:1) and dried at 50° C. under reduced pressure for 18 hrs to get solid TB21 (0.31 g)

Example 18

Crystallization of TB21 in MeOH:H$_2$O

TB21 (2 g, 56% assay, oil) was dissolved in MeOH:H$_2$O (5:1, 1 ml) by heating to 70° C. until homogenization. The solution was then allowed to cool to room temperature, and seeding was performed, causing precipitation. The mixture was stirred at room temperature for 18 hours, giving a slurry. The slurry was then cooled to −10° C. for 2 hours. The solid was then filtered under reduced pressure, washed with some drops of MeOH:H$_2$O (5:1) and dried at 50° C. under reduced pressure for 18 hrs to get solid TB21 (0.56 g)

Example 19

Crystallization of TB21 in Et$_2$O:MeOH

TB21 (2 g, 56% assay, oil) was suspended in Et$_2$O (5 ml) at 35° C. MeOH (0.5 ml) was added, causing dissolution. The solution was then allowed to cool to room temperature, and seeding was performed, not causing precipitation immediately. The solution was stirred at room temperature for 18 hours. After this time precipitation was observed. The slurry was then cooled to −10° C. for 5 hours. The solid was then filtered under reduced pressure, washed with some drops of Et$_2$O and dried at 50° C. under reduced pressure for 18 hrs to get solid TB21 (0.5 g)

Example 20

Crystallization of TB21 in Cellosolve

TB21 (2 g, 56% assay, oil) was dissolved in Cellosolve (2 ml) by heating to 90° C. until homogenization. The solution was then allowed to cool to room temperature, and seeding was performed, not causing precipitation immediately. The solution was stirred at room temperature for 18 hours. After this time precipitation was observed. The slurry was then cooled to −10° C. for 5 hours. The solid was then filtered under reduced pressure, washed with some drops of Cellosolve and dried at 50° C. under reduced pressure for 18 hrs to get solid TB21 (0.21 g)

Example 21

Crystallization of TB21 in MeOH:H$_2$O

TB21 (10 g, 56% assay, oil) was dissolved in a mixture MeOH:H$_2$O (5:1, 5 ml) by heating to 60° C. until homogenization. The solution was then allowed to cool to room temperature, and seeding was performed. The mixture was stirred at room temperature for 18 hours. The solid was then filtered under reduced pressure, washed with some drops of a mixture MeOH:H$_2$O (5:1) and dried at 50° C. under reduced pressure for 18 hrs to get solid TB21 (0.56 g)

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. All references mentioned herein are incorporated in their entirety.

What is claimed is:

1. A crystalline rosuvastatin intermediate having the following structure:

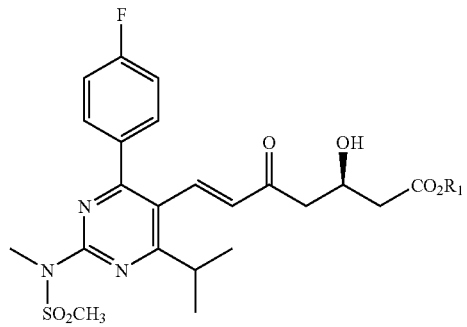

wherein R$_1$ in such crystalline rosuvastatin intermediate is a t-butyl group.

2. The crystalline rosuvastatin intermediate of claim 1, wherein the crystalline rosuvastatin intermediate has an X-Ray Diffraction pattern with peaks at 10.5, 13.1, 15.4, 19.0, and 20.4±0.2 degrees two theta.

3. The crystalline rosuvastatin intermediate of claim 2, further characterized by an X-Ray Diffraction pattern with peaks at 11.2, 15.7, 16.6, 18.0, 18.6, 19.4, 21.8, and 23.1±0.2 degrees two theta.

4. The crystalline rosuvastatin intermediate of claim 1, wherein the crystalline rosuvastatin intermediate has an FTIR spectrum with peaks at 1543, 1380, 1153, 961, and 847 cm$^{-1}$.

5. The crystalline rosuvastatin intermediate of claim 4, further characterized by an FTIR spectrum with peaks at: 2980, 1606, 1508, 1440, 1340, 1223, 1100, and 1065 cm cm$^{-1}$.

6. The crystalline rosuvastatin intermediate of claims 1, wherein the crystalline rosuvastatin intermediate has a DSC thermogram with an endothermic peak at about 100° C., and a broad endotherm at about 220° C.

7. A process for preparing the crystalline rosuvastatin intermediate of claim 1 comprising crystallizing the intermediate from a solution having at least one organic solvent.

8. The process of claim 7, wherein the organic solvent is a water miscible solvent.

9. The process of claim 8, wherein the water miscible solvent is in mixture with water.

10. The process of claim 9, wherein the water miscible solvent in a mixture with water is a mixture of MeOH/H$_2$O.

11. The process of claim 9, wherein the water miscible solvent in a mixture with water is a mixture of IPA/H$_2$O.

12. The process of claim 9, wherein the water miscible solvent in a mixture with water is a mixture of ethanol and water.

13. The process of claim 7, wherein crystallizing comprises heating a reaction mixture of the intermediate in the solvent to obtain a solution, followed by cooling.

14. The process of claim 7, wherein crystallizing comprises adding an anti-solvent to the solution.

15. The process of claim 14, wherein the antisolvent is selected from the group consisting of water, heptane, and hexane.

16. The process of claim 7, wherein crystallizing comprises seeding the solution.

17. The process of claim 7, wherein crystallizing comprises:
   a) heating a mixture comprising the intermediate and at least one organic solvent to obtain a solution;
   b) cooling the solution obtained in step (a);
   c) seeding the cooled solution; and
   d) recovering the crystalline intermediate.

18. The process of claim 17, further comprising cooling the solution both before and after seeding.

19. The process of claim 17, further comprising adding an antisolvent before the recovering step.

20. The process of claim 17, wherein heating is carried out to a temperature of about 40° C. to about 100° C.

21. The process of claim 17, wherein heating is carried out to a temperature of about 40° C. to about 70° C.

22. The process of claim 17, wherein cooling is carried out to a temperature of about −10° C. to about 20° C.

23. The process of claim 17, wherein the recovered crystalline rosuvastatin intermediate is dried at a temperature of about 40° C. to about 100° C.

24. The process of claim 17, wherein the solvent is selected from the group consisting of $C_6$ to $C_{12}$ aromatic and $C_5$ to $C_{12}$ aliphatic hydrocarbons, $C_3$ to $C_8$ ethers, $C_3$ to $C_8$ esters, $C_3$ to $C_8$ ketones, and $C_1$ to $C_5$ alcohols, and mixtures thereof.

25. The process of claim 17, wherein the solvent is selected from the group consisting of toluene, n-heptane, n-hexane, cyclohexane, cellosolve, ethyl acetate, n-butyl acetate, t-butyl acetate, methyl t-butyl ether, di-ethyl ether, tetrahydrofuran, methanol, ethanol, isopropanol, n-butanol, methyl iso-butyl ketone, diethyl, carbonate, butyl lactate, acetone, acetonitrile, and mixtures thereof.

26. The process of claim 17, wherein the solvent is toluene.

27. The process of claim 17, wherein the solvent is acetonitrile.

28. The process of claim 17, wherein crystallizing comprises:
   a) heating the solvent to a temperature of about 40° C. to about 70° C. to obtain a solution;
   b) cooling the solution obtained in step (a) to a temperature of about 20° C. to about 30° C.;
   c) seeding the cooled solution;
   d) cooling after seeding to a temperature of about −10° C. to about 20° C.; and
   e) recovering the crystalline intermediate.

* * * * *